(12) United States Patent
McKay et al.

(10) Patent No.: US 8,734,835 B2
(45) Date of Patent: *May 27, 2014

(54) COHESIVE OSTEOGENIC PUTTY AND MATERIALS THEREFOR

(75) Inventors: William F. McKay, Memphis, TN (US); Steven Marquis Peckham, Memphis, TN (US); Jeffrey L. Scifert, Arlington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 637 days.

This patent is subject to a terminal disclaimer.

(21) Appl. No.: 13/015,953

(22) Filed: Jan. 28, 2011

(65) Prior Publication Data

US 2011/0165215 A1  Jul. 7, 2011

Related U.S. Application Data

(63) Continuation of application No. 11/345,605, filed on Feb. 1, 2006, now Pat. No. 7,939,092.

(51) Int. Cl.
*A61F 2/28* (2006.01)

(52) U.S. Cl.
USPC ................................ 424/426; 623/11.11

(58) Field of Classification Search
CPC ...... A61F 2002/2835; A61F 2/28; A61F 2/50
See application file for complete search history.

(56) References Cited

U.S. PATENT DOCUMENTS

| | | | |
|---|---|---|---|
| 4,776,890 A | 10/1988 | Chu | |
| 5,356,629 A | 10/1994 | Sander et al. | |
| 5,531,791 A | 7/1996 | Wolfinbarger, Jr. | |
| 5,739,286 A | 4/1998 | Silver et al. | |
| 6,679,918 B1 | 1/2004 | Benedict et al. | |
| 2002/0076429 A1 | 6/2002 | Wironen et al. | |
| 2002/0082694 A1 | 6/2002 | McKay | |
| 2003/0236573 A1 | 12/2003 | Evans et al. | |
| 2003/0236578 A1* | 12/2003 | Gammerman et al. | 700/47 |
| 2004/0002558 A1* | 1/2004 | McKay | 523/115 |
| 2004/0138758 A1 | 7/2004 | Evans et al. | |
| 2005/0186240 A1 | 8/2005 | Ringeisen et al. | |

FOREIGN PATENT DOCUMENTS

WO  0215881 A2  2/2002

OTHER PUBLICATIONS

Internet pages, Healthcare Sales & marketing Network News: Kensey Nash Announces Launch of New Product . . . , http://salesandmarketinqnetwork.com/news release.php?ID=2005433&kev=Orthovita; 3 pages, last printed Nov. 1, 2005.

Internet pages, Orthovita Products: VITOSS Technical Specifications: Description, http://www.orthovita.com/products/vitoss/techspecs.html, 8 pages, last printed Nov. 1, 2005.

* cited by examiner

*Primary Examiner* — Carlos Azpuru
(74) *Attorney, Agent, or Firm* — Sorell Lenna & Schmidt LLP

(57) ABSTRACT

Described is an implantable medical material comprising a malleable, cohesive, shape-retaining putty including mineral particles, insoluble collagen fibers and soluble collagen. The medical material can be used in conjunction with biologically active factors such as osteogenic proteins to treat bone or other tissue defects in patients.

10 Claims, 8 Drawing Sheets

COHESIVE OSTEOGENIC PUTTY AND MATERIALS THEREFOR

CROSS REFERENCE TO RELATED APPLICATION

This application is a continuation of U.S. application Ser. No. 11/345,605, filed Feb. 1, 2006, the entirety of which is incorporated by reference.

BACKGROUND OF THE INVENTION

The present invention relates generally to medical putty implant materials, and in certain aspects to collagenous medical putty implant materials.

A variety of materials have been suggested for the treatment of bone defects. In addition to traditional bone grafting, a number of synthetic bone graft substitutes have been used or explored, including several putty materials.

To conduct bone through-growth effectively, implant materials derive benefit from the presence of substantial scaffolding material such as biocompatible ceramics or other mineral scaffolds. Such mineral materials are generally hard, brittle substances. The incorporation of substantial levels of mineral particles into putty materials, particularly in respect of granules or other relatively large particles, proves difficult because the large pieces of hard mineral tend to disrupt the putty mass such that it is readily broken or eroded away, and lacks cohesiveness desired for handling prior to implant and for persistence after implant. This may present problems in achieving effective bone growth into and through the desired implant volume, due to migration or separation of the scaffolding particulates.

In view of the background in the area, there exist needs for improved putty materials which not only have high levels of incorporated, relatively large mineral particles, but also maintain the desired combination of malleability and cohesiveness. In certain aspects, the present invention is directed to these needs.

SUMMARY OF THE INVENTION

Accordingly, in one aspect, the present invention is directed to an implantable osteogenic medical material comprising a malleable, cohesive, shape-retaining putty that includes a combination of mineral particles and collagen, wherein the collagen includes insoluble collagen fibers and an equal or relatively lesser amount by weight of soluble collagen. Thus, in one embodiment, the invention provides a malleable, cohesive, shape-retaining putty that comprises 60% to 75% by weight of an aqueous liquid medium and includes a bone morphogenic protein incorporated at a level of about 0.6 milligrams per cubic centimeter (mg/cc) to about 2 mg/cc. The putty includes mineral particles dispersed therein having an average particle diameter in the range of 0.4 millimeters (mm) to 5 mm at a level of 0.25 g/cc to 0.35 g/cc in the overall putty. The putty further includes insoluble collagen fibers at a level of 0.04 g/cc to 0.1 g/cc, and soluble collagen at a level of 0.01 g/cc to 0.08 g/cc, with the further proviso that the weight ratio of insoluble collagen fibers to soluble collagen in the putty is in the range of 4:1 to 1:1.

In another embodiment, the invention provides an implantable medical material comprising a malleable, cohesive, shape-retaining putty comprised 60% to 75% by weight of an aqueous liquid medium, and dispersed mineral particles having an average particle diameter in the range of 0.4 mm to 5 mm at a level of 0.25 g/cc to 0.35 g/cc. The putty also includes insoluble collagen fibers at a level of 0.04 g/cc to 0.1 g/cc, and soluble collagen at a level of 0.01 g/cc to 0.08 g/cc, with the proviso that the weight ratio of insoluble collagen fibers to soluble collagen is in the range of 4:1 to 1:1. Such putty can be used as an osteoconductive material, for example in bone void filler applications, and/or can be modified to incorporate one or more osteogenic proteins to provide an osteogenic putty.

In another embodiment, the invention provides a method for preparing an implantable medical putty material. The method includes providing a dry, porous material that includes a particulate mineral material having an average particle diameter of about 0.4 mm to about 5 mm embedded within a disruptable collagenous matrix. The dried material is comprised 70% to 90% by weight of the particulate ceramic material and 10% to 30% by weight of collagen. The collagenous matrix includes insoluble collagen fibers and soluble collagen present in a weight ratio of 4:1 to 1:1. The method includes the further step of applying an amount of aqueous medium to the dried material and disrupting the collagenous matrix so as to prepare a malleable, cohesive, shape-retaining putty that comprises 60% to 75% by weight of water. In certain aspects of this embodiment, the aqueous medium can include a bone morphogenic protein dissolved therein at a level of about 0.6 mg/cc to about 2 mg/cc, so as to result in an implantable osteogenic medical material.

In still another embodiment, the invention provides an implant material that comprises a dried porous body including a particulate ceramic material having an average particle diameter of 0.4 mm to 5 mm embedded within a disruptable collagenous matrix, wherein the body comprises 70% to 90% by weight of the particulate mineral material and 10% to 30% by weight of collagen. The collagenous matrix includes insoluble collagen fibers and soluble collagen, wherein the insoluble collagen fibers and soluble collagen are present in a weight ratio of 4:1 to 1:1. The dried porous body is wettable with a biocompatible aqueous liquid to form a malleable, cohesive, shape-retaining putty material that includes an admixture of the collagen fibers, aqueous collagen gel, and the particulate mineral material.

In still further embodiments, the present invention provides methods for treating patients that involve implanting in the patients a medical material as described herein.

Additional embodiments as well as features and advantages of the present invention will be apparent to those of ordinary skill in the art from the descriptions herein.

DETAILED DESCRIPTION

Figure 1:
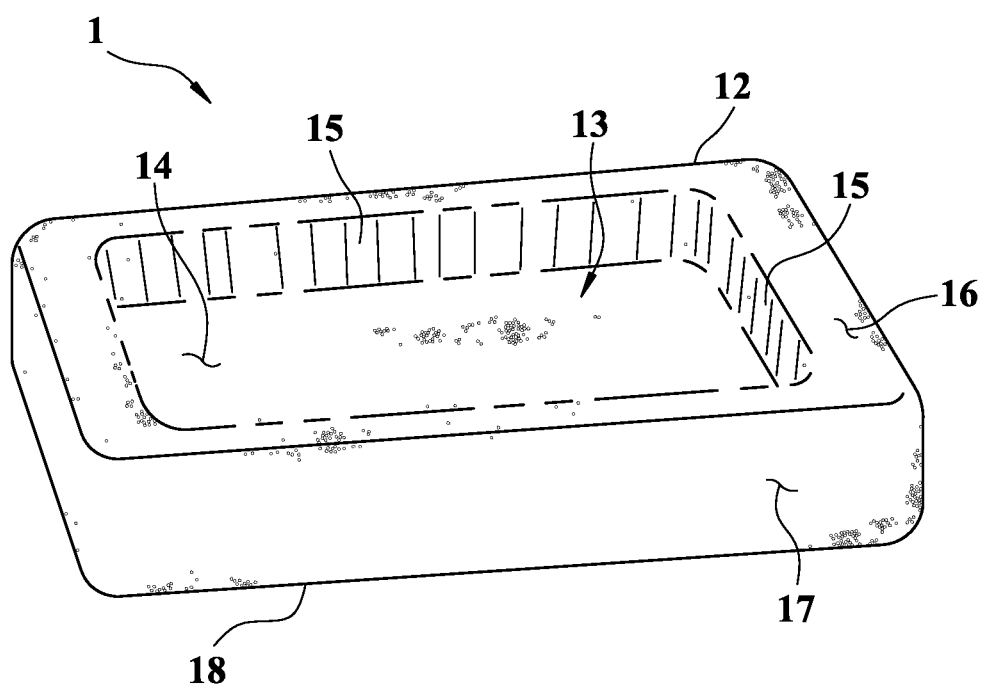
FIG. 1 provides a perspective view of a dried porous body implant material of the invention including a reservoir for receipt of a wetting liquid.

For the purposes of promoting an understanding of the principles of the invention, reference will now be made to certain embodiments and specific language will be used to describe the same. It will nevertheless be understood that no limitation of the scope of the invention is thereby intended, such alterations and further modifications in the illustrated device, and such further applications of the principles of the invention as described herein being contemplated as would normally occur to one skilled in the art to which the invention relates.

As disclosed above, in certain aspects, the present invention relates to implantable osteogenic medical putty, and to methods and materials that are useful for preparing such an osteogenic medical putty. Preferred medical putty materials of the invention possess a combination of advantageous properties including high mineral content, malleability, cohesiveness, and shape retention. In this regard, as used herein the term "malleable" means that the material is capable of being permanently converted from a first shape to a second shape by the application of pressure. The term "cohesive" as used herein means that the putty tends to remain a singular, connected mass upon stretching, including the exhibition of the ability to elongate substantially without breaking upon stretching. In the context of putties of the invention containing insoluble collagen fibers and soluble collagen, upon stretching, the advantageous putties exhibit elongation, during which the existence of substantial levels of intermeshed collagen fibers clinging to one another becomes apparent. As used herein, the term "shape-retaining" means that the putty material is highly viscous and unless acted upon with pressure tends to remain in the shape in which it is placed. This is contrasted to thinner paste form materials which readily flow, and thus would pool or puddle upon application to a surface. In certain features of the invention, novel combination of ingredients provide a medical putty material that not only contains a significant, high level of large particulate mineral particles, but also exhibits superior properties with respect to malleability, cohesiveness, and shape retention.

Putties according to aspects of the present invention will include a combination of soluble collagen and insoluble collagen. "Soluble collagen" refers to the solubility of individual tropocollagen molecules in acidic aqueous environments. Tropocollagen may be considered the monomeric unit of collagen fibers and its triple helix structure is well recognized. "Insoluble collagen" as used herein refers to collagen that cannot be dissolved in an aqueous alkaline or in any inorganic salt solution without chemical modification, and includes for example hides, splits and other mammalian or reptilian coverings. For example, "natural insoluble collagen" can be derived from the corium, which is the intermediate layer of an animal hide (e.g. bovine, porcine, etc.) that is situated between the grain and the flesh sides. "Reconstituted collagen" is essentially collagen fiber segments that have been depolymerized into individual triple helical molecules, then exposed to solution and then reassembled into fibril-like forms.

The collagen putty of the preferred embodiment of the present invention contains both soluble collagen and insoluble collagen fibers. The soluble collagen and insoluble collagen fibers can first be prepared separately, and then combined. Both the soluble collagen and the insoluble collagen fibers can be derived from bovine hides, but can also be prepared from other collagen sources (e.g. bovine tendon, porcine tissues, recombinant DNA techniques, fermentation, etc.).

In certain embodiments, the invention provides putty-form compositions that include the insoluble collagen fibers at a level of 0.04 g/cc to 0.1 g/cc of the putty, and soluble collagen at a level of 0.01 g/cc to 0.08 g/cc of the putty. In other embodiments, such compositions include insoluble collagen fibers at a level of about 0.05 to 0.08 g/cc in the putty, and soluble collagen at a level of about 0.02 to about 0.05 g/cc in the putty. In general, putties of the invention will include insoluble collagen fibers in an amount (percent by weight) that is at least equal to or greater than the amount of soluble collagen, to contribute beneficially to the desired handling and implant properties of the putty material. In advantageous embodiments, the collagenous matrix will include insoluble collagen fibers and soluble collagen present in a weight ratio of 4:1 to 1:1, more advantageously about 75:25 to about 60:40. Further still, additional desired putties of the invention include the insoluble collagen fibers and soluble collagen in a weight ratio of about 75:25 to about 65:35, and in one specific embodiment about 70:30.

Medical putties of the present invention also include an amount of a particulate mineral material. In certain aspects of the invention, the particulate mineral is incorporated in the inventive putty composition at a level of at least about 0.25 g/cc of putty, typically in the range of about 0.25 g/cc to about 0.35 g/cc. Such relatively high levels of mineral will be helpful in providing a scaffold for the ingrowth of new bone.

The mineral used in the present invention can include a natural or synthetic mineral that is effective to provide a scaffold for bone ingrowth. Illustratively, the mineral matrix may be selected from one or more materials from the group consisting of bone particles, Bioglass®, tricalcium phosphate, biphasic calcium phosphate, hydroxyapatite, corraline hydroxyapatite, and biocompatible ceramics. Biphasic calcium phosphate is a particularly desirable synthetic ceramic for use in the invention. Such biphasic calcium phosphate can have a tricalcium phosphate:hydroxyapatite weight ratio of about 50:50 to about 95:5, more preferably about 70:30 to about 95:5, even more preferably about 80:20 to about 90:10, and most preferably about 85:15. The mineral material can be particulate having an average particle diameter between about 0.4 and 5.0 mm, more typically between about 0.4 and 3.0 mm, and desirably between about 0.4 and 2.0 mm.

In another aspect of the invention, the mineral material can include bone particles, possibly cancellous but preferably cortical, ground to provide an average particle diameter among those discussed above for the particulate mineral material. Both human and non-human sources of bone are suitable for use in the instant invention, and the bone may be autographic, allographic or xenographic in nature relative to the mammal to receive the implant. Appropriate pre-treatments known in the art may be used to minimize the risks of disease transmission and/or immunogenic reaction when using bone particles as or in the mineral material.

In one embodiment, xenogenic bone that has been pre-treated to reduce or remove its immunogenicity is used in or as the porous mineral matrix in the implant composition. For example, the bone can be calcined or deproteinized to reduce the risks of immunogenic reactions to the implant material.

A putty-form composition of the invention can include a significant proportion of a liquid carrier, which will generally be an aqueous liquid such as water, saline, or buffered solutions. In one aspect, a malleable, cohesive, shape-retaining putty of the invention comprises about 60% to 75% by weight of an aqueous liquid medium, such as water, advantageously about 65% to 75% by weight of an aqueous liquid medium (e.g. water).

Putty-form compositions can also include a bone morphogenic protein incorporated therein in an effective amount to render the putty osteogenic when implanted in a mammal, such as a human patient. In one embodiment, an inventive putty composition includes bone morphogenic protein at a level of about 0.6 milligrams per cubic centimeter (mg/cc) of putty to about 2 mg/cc of putty, advantageously at a level of about 0.8 mg/cc to about 1.8 mg/cc.

As noted above, the compositions of the invention will generally incorporate at least as much insoluble collagen fiber as soluble collagen on a weight basis, e.g. in a weight ratio of about 4:1 to about 1:1. Advantageous putty compositions will include more insoluble collagen fibers than soluble collagen, for instance, in a weight ratio of about 75:25 to about 60:40, more desirably about 75:25 to about 65:35, and in one specific embodiment about 70:30. Suitable collagen materials for these purposes can be prepared using techniques known in the literature or can be obtained from commercial sources, including for example from Kensey Nash Corporation (Exton, Pa.) which manufactures soluble collagen known as Semed S, fibrous collagen known as Semed F, and a composite collagen known as P1076.

Any suitable osteogenic material can be used in methods and/or compositions of the invention, including for instance harvested autologous bone or other suitable osteogenic substances. In certain embodiments, the osteogenic substance can include a growth factor that is effective in inducing formation of bone. Desirably, the growth factor will be from a class of proteins known generally as bone morphogenic proteins (BMPs), and can in certain embodiments be recombinant human (rh) BMPs. These BMP proteins, which are known to have osteogenic, chondrogenic and other growth and differentiation activities, include rhBMP-2, rhBMP-3, rhBMP4 (also referred to as rhBMP-2B), rhBMP-5, rhBMP-6, rhBMP-7 (rhOP-1), rhBMP-8, rhBMP-9, rhBMP-12, rhBMP-13, rhBMP-15, rhBMP-16, rhBMP-17, rhBMP-18, rhGDF-1, rhGDF-3, rhGDF-5, rhGDF-6, rhGDF-7, rhGDF-8, rhGDF-9, rhGDF-10, rhGDF-11, rhGDF-12, rhGDF-14. For example, BMP-2, BMP-3, BMP-4, BMP-5, BMP-6 and BMP-7, disclosed in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in U.S. Pat. No. 5,637,480; BMP-11, disclosed in U.S. Pat. No. 5,639,638, or BMP-12 or BMP-13, disclosed in U.S. Pat. No. 5,658,882, BMP-15, disclosed U.S. Pat. No. 5,635,372 and BMP-16, disclosed in U.S. Pat. Nos. 5,965,403 and 6,331,612. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of all of these patents and applications are hereby incorporated herein by reference. Also useful in the present invention are heterodimers of the above and modified proteins or partial deletion products thereof. These proteins can be used individually or in mixtures of two or more. rhBMP-2 is preferred.

The BMP may be recombinantly produced, or purified from a protein composition. The BMP may be homodimeric, or may be heterodimeric with other BMPs (e.g., a heterodimer composed of one monomer each of BMP-2 and BMP-6) or with other members of the TGF-beta superfamily, such as activins, inhibins and TGF-beta 1 (e.g., a heterodimer composed of one monomer each of a BMP and a related member of the TGF-beta superfamily). Examples of such heterodimeric proteins are described for example in Published PCT Patent Application WO 93/09229, the specification of which is hereby incorporated herein by reference. The amount of osteogenic protein useful herein is that amount effective to stimulate increased osteogenic activity of infiltrating progenitor cells, and will depend upon several factors including the size and nature of the defect being treated, and the carrier and particular protein being employed. In certain embodiments, the amount of osteogenic protein to be delivered will be in a range of from about 0.05 to about 1.5 mg.

Other therapeutic growth factors or substances may also be used in putties of the present invention, especially those that may be used to stimulate bone formation. Such proteins are known and include, for example, platelet-derived growth factors, insulin-like growth factors, cartilage-derived morphogenic proteins, growth differentiation factors such as growth differentiation factor 5 (GDF-5), and transforming growth factors, including TGF-$\alpha$ and TGF-$\beta$. As well, other biologically-derived matrix materials such as demineralized bone matrix (DBM) may be incorporated into putties of the invention.

The osteogenic proteins or other biologically active agents to be used in the present invention can be provided in liquid formulations, for example buffered aqueous formulations. In certain embodiments, such formulations are mixed with, received upon and/or within, or otherwise combined with a dried implant material in order to prepare an osteogenic putty material of the invention.

As further enhancements of the compositions of the present invention, those skilled in the art will readily appreciate that other osteogenic enhancing factors may be incorporated into the composition. Such additional factors include, but are not limited to host compatible osteogenic progenitor cells, autographic bone marrow, allographic bone marrow, transforming growth factor-beta, fibroblast growth factor, platlet derived growth factor, insulin-like growth factor, microglobulin-beta, antibiotics, antifungal agents, wetting agents, glycerol, steroids and non-steroidal anti-inflammatory compounds.

In another aspect, the present invention provides a dried implant material that can be combined with an appropriate amount of an aqueous medium in order to prepare putty materials of the invention. The dried implant material will be a porous body that includes a particulate mineral material having an average particle diameter of about 0.4 mm to about 5.0 mm embedded within a disruptable collagenous matrix. The dried, porous implant material will be comprised 70% to 90% by weight of the particulate mineral material and 10% to 30% by weight of collagen. The collagenous matrix will include insoluble collagen fibers and soluble collagen present in a weight ratio as discussed above, that is, 4:1 to 1:1, advantageously about 75:25 to about 60:40, more advantageously about 75:25 to about 65:35, and in one specific embodiment about 70:30. In addition, as discussed above, the particulate mineral material will typically have an average particle diameter between 0.4 and 3.0 mm, and more desirably between 0.4 and 2.0 mm.

The dried, porous body can have a density of between about 0.1 g/cc to about 0.3 g/cc, more desirably between about 0.15 g/cc and about 0.25 g/cc, and in certain aspects between about 0.18 g/cc and about 0.25 g/cc. Such dried, porous implant bodies can also exhibit porosities of at least about 50%, more desirably at least about 70% up to about 90%, and in certain embodiments in the range of about 80% to about 90%.

The dried, porous implant bodies in accordance with the invention can be provided in any suitable shape, including cylinders, cubes, or other shapes. In certain aspects, the dried, porous implant body can define a reservoir for receiving amounts of a wetting liquid, e.g. to be used in the preparation of a putty from the dried implant material.

The dried porous body can be prepared using any suitable technique, including for example casting a liquid medium containing the dry ingredients, and then drying that medium by any appropriate means such as air drying or lyophilization.

With reference to FIG. 1, depicted is an illustrative, dried porous implant body 11 of the invention. The body 11 has a cast material 12 which defines a reservoir 13. The reservoir 13 has a bottom surface 14 and side walls 15, and can hold a liquid to be used to wet the body 11 in the formation of a putty, such that the liquid can be conveniently charged to reservoir 13 and allowed to soak into body 11 over time. The body 11 has an upper surface 16 surrounding the reservoir 13, as well as sidewalls 17 and a bottom surface 18.

Figure 2:
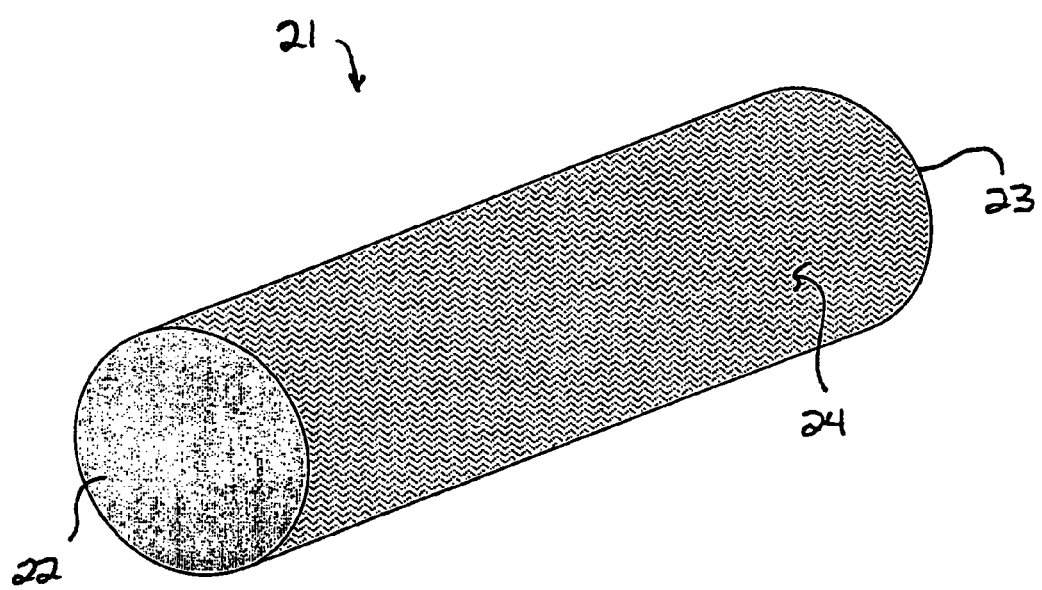
FIG. 2 provides a perspective view of a cylindrical-form dried porous body implant material of the invention.

Referring to FIG. 2, shown is another dried, porous implant body 21 according to one embodiment of the invention. Implant body 21 is cylindrical in shape, having a circular cross section. Implant body 21 is thus conveniently shaped for receipt within a cylindrical syringe barrel of a roughly corresponding or greater cross sectional dimension. Implant body 21 includes a first end 22, a second end 23, and a smooth, rounded external surface 24.

In use, the dried, porous body (e.g. 11, 21) can be combined with a sufficient amount of a liquid material such as an aqueous medium to prepare a putty form material as described herein. The body (11, 21) will exhibit a disruptable character, such that it can be broken down by physical manipulation (e.g. manual crushing and kneading) to form a putty when combined with a liquid. Thus, chemical, covalent cross linking between the collagen materials in the dried material, if any, will generally be minimal. Other modes of providing integrity to the body (11, 21) can be used, e.g. dehydrothermal cross linking, or cross linking or adhesive forces imparted by ionic or hydrogen bonding. It will thus be understood that cross linking can be present in the dried, porous body (11, 21), but that it will be of such a nature to leave the body disruptable to form a putty as described herein.

Typically, the combination of a dried porous implant body of the invention with the liquid carrier, and the physical kneading or other mixing of the resultant mass, will result in a reduction of the volume of the dried porous body, for example resulting in a putty volume that is about 30% to about 70% of that of the original implant body, more typically about 40% to about 60%. This is a result of a breakdown of the original porosity of the dried implant body to form a relatively less porous or non-porous putty implant composition. The liquid carrier will typically be an aqueous substance, including for instance sterile water, physiological saline, blood, bone marrow, bone marrow fractions or other solutions (with or without organic co-solvents), emulsions or suspensions that provide adequate wetting characteristics to form putties of the invention.

In use, the putty implant compositions of the invention are implanted at a site at which bone growth is desired, e.g. to treat a disease, defect or location of trauma, and/or to promote artificial arthrodesis. The putty form of the compositions enables their positioning, shaping and/or molding within voids, defects or other areas in which new bone growth is desired. In particularly advantageous embodiments, the shape-retaining property of the putty material of the invention will desirably provide sufficient three-dimensional integrity to resist substantial compression when impinged by adjacent soft tissues of the body at a bony implant site.

Bone repair sites that can be treated with medical putty compositions of the invention include, for instance, those resulting from injury, defects brought about during the course of surgery, infection, malignancy or developmental malformation. The putty compositions can be used in a wide variety of orthopedic, periodontal, neurosurgical and oral and maxillofacial surgical procedures including, but not limited to: the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the isolate or implant comprising the isolate include, but are not limited to: the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

Once in place, osteogenic putty form implant compositions of the invention can effectively induce and support the ingrowth of bone into the desired area even in a primate subject such as a human exhibiting a relatively slow rate of bone formation compared to smaller mammals, for example rodents or rabbits.

Osteogenic putty compositions of the invention are especially advantageous when used in bones or bone portions that are vascularized to only moderate or low levels. These areas present particularly low rates of bone formation, and as such the rapid resorption of the carrier poses enhanced difficulties. Examples of moderate or only slightly vascularized sites include, for example, transverse processes or other posterior elements of the spine, the diaphysis of long bones, in particular the mid diaphysis of the tibia, and cranial defects. An especially preferred use of paste compositions of the invention is as an implant to promote arthrodesis between vertebrae in spinal fusions in humans or other mammals, including for example interbody, posterior and/or posterolateral fusion techniques. Illustratively, as set forth in Example 3 below, osteogenic putty compositions containing recombinant human BMP-2 were used successfully in posterolateral fusion procedures, achieving highly beneficial arthodesis as examined by both radiographic and biomechanical techniques, comparing very favorably to autograft bone (long considered the "gold standard" in such fusions).

In addition, in accordance with other aspects of the invention, the putty compositions of the invention can be incorporated in, on or around a load-bearing spinal implant (e.g. having a compressive strength of at least about 10000 N) implant device such as a fusion cage, dowel, or other device having a pocket, chamber or other cavity for containing an osteogenic composition, and used in a spinal fusion such as an interbody fusion. One illustrative such use is set forth in Example 2 below, in which an inventive osteogenic putty was used in conjunction with a load-bearing interbody spinal spacer to achieve a highly successful interbody fusion, again comparing very favorably to autograft bone.

Medical putty compositions of the present invention can also be used in combination with cells, including for instance progenitor and/or stem cells derived from embryonic or adult tissue sources and/or taken from culture. Illustratively, putties of the invention can incorporate cells derived from blood, bone marrow, or other tissue sources from the patient to be treated (autologous cells) or from a suitable allogenic or xenogenic donor source. In certain embodiments of the invention, putties of the invention incorporate an enriched bone marrow fraction, prepared for example as described in US Patent Publication No. 2005/0130301 to McKay et al. published Jun. 16, 2005, publishing U.S. patent application Ser. No. 10/887,275 filed Jul. 8, 2004, which is hereby incorporated herein by reference in its entirety. Thus, putty materials can incorporate a bone marrow fraction enriched in connective tissue growth components, that is prepared by centrifuging a biological sample (e.g. from the patient to be treated) to separate the sample into fractions including a fraction rich in connective tissue growth components. The fraction rich in connective tissue growth components can then be isolated from the separated sample, and incorporated into the putty material of the present invention, e.g. by using the fraction in or as the wetting medium for the dried, porous body as discussed hereinabove.

The present invention also provides medical kits that can be used to prepare implant compositions. Such kits can include a dried, porous body according to the invention, along with an aqueous medium for combination with the body to form a putty and/or another item such as a load-bearing implant (e.g. a spinal spacer) and/or an osteogenic substance such as a BMP. In one specific form, such a medical kit will include the dried, porous body, a BMP in lyophilized form (e.g. rhBMP-2), and an aqueous medium for reconstitution of the BMP to prepare an aqueous formulation that can then be combined with the dried, porous body to prepare an osteogenic putty of the invention.

The invention will now be more particularly described with reference to the following specific Examples. It will be understood that these Examples are illustrative and not limiting of the invention.

EXAMPLE 1

Preparation of Inventive Putty with rhBMP-2

9 ml of a buffered aqueous solution of rhBMP-2 (1.5 mg/ml solution, as available with INFUSE® Bone Graft, Medtronic Sofamor Danek, Memphis, Tenn.) were added to a dried, porous cylindrical body having a volume of 18 cc and weighing approximately 3.8 grams. The dried, porous body had been prepared by casting and then lyophilizing an aqueous suspension of insoluble collagen fibers, acid soluble collagen, and ceramic granules, exhibited a porosity of about 85%, and was comprised of the following:

| Material | Wt % Solids |
|---|---|
| Biphasic CaP Granules* | 80% |
| Insoluble Collagen Fibers | 14% |
| Acid Soluble Collagen | 6% |

*Mastergraft ® Ceramic Granules, biphasic calcium phosphate granules containing 85% tricalcium phosphate and 15% hydroxyapatite, particle size 0.5-1.6 mm, After soaking, the implant material and added rhBMP-2 solution were thoroughly mixed by kneading to prepare approximately 10 cc of an implantable putty material comprised about 70% by weight of water and containing about 0.3 g/cc biphasic calcium phosphate ceramic granules, 0.05 g/cc insoluble collagen fibers, 0.02 g/cc acid soluble collagen, and 1.5 mg/cc of rhBMP-2. The resulting osteogenic putty exhibited superior properties for handling and use. The putty retained its shape unless acted upon, and formed a malleable, cohesive, fibrous mass with entrained granules, that would elongate without breaking upon stretching.

EXAMPLE 2

Use of Inventive Putty in Interbody Spinal Fusions

An ovine interbody fusion model was used to compare the ability of a 5 mm×11 mm×11 mm polyetheretherketone spinal spacer (VERTE-STACK® CORNERSTONE® PSR PEEK Implant, Medtronic Sofamor Danek, Memphis, Tenn.) with packed-in Autograft and the PEEK spacer with packed-in Inventive Putty of Example 1 (IP+rhBMP-2) to effect interbody fusion at 6 months post-operatively. The efficacy of these treatments to induce interbody fusion in the ovine lumbar fusion model using blinded radiographic, biomechanical, and histologic measures was evaluated. Assessment of fusion was made with Faxitron high-resolution radiography, non-destructive biomechanical testing, and undecalcified histology with corresponding microradiography. All analyses were conducted in a blinded fashion. In addition, undecalcified histology was used to evaluate the osteocompatibility of the Inventive Putty. In addition to the treatment groups being evaluated, normal spines were evaluated using the same methodology. When all data acquisition was complete, the key was broken, and radiographic, biomechanical, and histologic data were analyzed by treatment group.

Animal Model:

The sheep lumbar spine model was used because of the biomechanical similarities between the sheep and human lumbar spine. Wilke et al. characterized the biomechanical parameters (range of motion, neutral zone, and level stiffness) of sheep spines and made comparisons with data from human specimens previously published by White and Panjabi (see, Wilke et al., *Spine:* 22(20): 2365-2374, 1997; and White AA and Panjabi MM, editors, Clinical Biomechanics of the Spine, 2nd ed., J. B. Lippincott, Philadelphia, Pa., 1990). Wilke et al. found that the "ranges of motion of sheep spines for the different load directions are qualitatively similar in their craniocaudal trends to those of human specimens reported in the literature." They further concluded that: "Based on the biomechanical similarities of the sheep and human spines demonstrated in this study, it appears that the sheep spine . . . can serve as an alternative for the evaluation of spinal implants.

Surgical Technique:

Upon arrival at the facility, the 12 sheep were placed in the appropriate pastures of the large animal research barn. They were dewormed and eartagged for identification. Physical examination was performed and any animals with signs of respiratory disease had venous blood submitted for a complete blood count (CBC).

The sheep were anesthetized. Wool was removed from the dorsal lumbar area and the sheep positioned in sternal recumbency on the operating table.

Iliac Crest Autograft Harvesting: Autograft was used as a control. The following protocol was followed. The dorsal and dorsolateral lumbar and iliac crest areas were prepared for aseptic surgery with multiple scrubs of povidone-iodine alternated with isopropyl alcohol. The area was draped and a 3-cm incision made over the left iliac crest. Following partial reflection of the gluteal muscles. An osteotome was used to create a small window in the craniodorsal face of the iliac crest. Using a curette, about 2 cc of autogenous cancellous bone was removed, and was later packed into one of the implants (e.g. PEEK spacer) used for the lumbar fusion (this is the control case). Intralesional morphine sulfate was administered prior to closure of the iliac crest incision. The iliac crest site was closed routinely using 2/0 polysorb for the subcutaneous tissues and stainless steel staples for the skin.

Ventral ("Anterior") Interbody Fusion: The dorsal and dorsolateral lumbar area was prepared for aseptic surgery with multiple scrubs of povidone-iodine alternated with isopropyl alcohol. The area was draped and a ventrolateral retroperitoneal approach to L3/L4 and L5/L6 through the oblique abdominal muscles to the plane ventral to the transverse processes was made.

Implant insertion: The bone graft from the iliac crest or a bone graft substitute that was being investigated (rhBMP-2+ Putty), was placed into the PEEK spacer (~1.5 cc of material) and implanted into the disc space, following preparation of the endplates.

Wound Closure: Routine closure of external abdominal muscular fascia (0 Polysorb (absorbable suture), subcutaneous tissue (2/0 Polysorb and skin (2/0 monofilament non-absorbable suture) was performed. Operative time for each animal was usually about 40 minutes. Perioperative antibiotics (Cephazolin sodium) were administered. Postoperative radiographs were performed while the sheep were still under general anesthesia.

Aftercare: Immediately after surgery, the sheep were transferred from the operating table to a modified wheelbarrow and while still under general anesthesia, taken to a radiology suite where dorsoventral and lateral radiographs of the fusion sites were obtained. Following radiographic evaluation, while still in the modified wheelbarrow, they were observed until the swallowing reflex returned. At that point they were extubated and taken to a trailer where they were propped in sternal recumbency. At the end of the day, all animals that were operated upon that day were moved to research pastures. The sheep were housed outdoors (with access to a three-sided shelter) for the convalescence and allowed to exercise at will. Postoperative analgesia was provided as described. The sheep were anesthetized and radiographed at three months posoperatively.

Euthanasia: After 6 months postoperatively, the 12 sheep were euthanized in a humane manner. Euthanasia was performed according to the guidelines set forth by the AVMA Panel on Euthanasia (J. Am. Vet. Med. Assoc., 202:229-249, 1993). Radiographs of the lumbar fusion sire were taken in these sheep to evaluate the degree of fusion at L3-L4.

Specimen Collection and Handling: Following euthanasia, a complete gross necropsy was conducted on all 12 animals. Conventional gross examination of all major organ systems and histopathological evaluation of any pathological lesions was performed. Animals that died or were prematurely euthanized during the course of the study had a complete necropsy performed to determine the cause of disease or death. At necropsy the lumbar vertebrae that were fused were harvested.

Material Analysis: All samples from the lumbar area from the sheep were subjected to mechanical testing of the fusion sites. They were tested for stiffness to saggital and coronal plan bending moments (flexion, extension, right and left lateral bending). As these mechanical tests were nondestructive, the fusion sites were also examined histologically.

Implant Materials:

Twelve treated spinal levels (L4-L5) were evaluated. The study groups are defined below.

| Study Group | No. of Samples (N) |
| --- | --- |
| Autograft Interbody w/PEEK spacer (Autograft + PEEK) | 6 |
| Inventive Putty Interbody + rhBMP-2 w/PEEK spacer (IP + BMP2 + PEEK) | 6 |
| Normal Intact | 17 |
| Total | 29 |

After the survival phase of the study was completed, the spines were immediately frozen for evaluation.

Methods of Analysis:

1. Ex-vivo Biomechanical Testing of the Treated Lumbar Motion Segment:

Flexibility Testing

Unconstrained biomechanical testing was performed in a non-destructive manner on all spines after the frozen specimens were thawed. All tests were performed within 12 hours of specimen thawing. Specimens were only frozen once. Instrumentation applied to the anterior part of the vertebral body was removed prior to biomechanical testing so that only the stiffness of the spine and fusion mass construct was tested, not the instrumentation. Flexibility of the motion segments was determined in flexion, extension, right and left lateral bending, and right and left axial rotation. The purpose of the biomechanical testing was to quantify the stiffness of the lumbar motion segments augmented with the previously described interbody fusion treatments. The treated (L4-L5) motion segments were dissected from the harvested lumbar spines and cleaned of extraneous soft tissues leaving the ligamentous and osseous tissues intact. Specially designed loading and base frames were secured on the L4 and L5 vertebra, respectively.

Moments of 0, 0.5, 2.5, 4.5, 6.5, and 8.5 Nm were achieved in each loading direction. Static loads were used to apply the pure moments. Three markers reflecting the infrared light were attached to each vertebra. The locations of the infrared reflective markers will be recorded using three VICON cameras (ViconPeak, Oxford, England) at each load. Three-dimensional load-displacement data were then acquired with pure moments applied in flexion, extension, left and right lateral bending, and left and right axial rotation. Basic principles of using 3-D motion analysis system for investigating the 3-D load-displacement behavior are well known in the literature.

Biomechanics data from a normal (untreated) intact group of sheep lumbar spine motion segments that have been obtained previously were used as baseline data for normal lumbar spine motion for L4-L5 in sheep. Differences in the stiffness (flexibility) between groups and the normals were statistically compared. Non-parametric Kruskal-Wallis and Mann-Whitney tests were used to analyze the biomechanics data.

2. Radiographic Assessment:

Radiographs were taken immediately after surgery (AP and lateral views), at regular post-operative intervals (AP and lateral views), and at the time of sacrifice (AP and lateral views). A high-resolution radiography unit (Faxitron, Hewlett Packard, McMinnville, Oreg.) and high-resolution film (EKTASCAN B/RA Film 4153, Kodak, Rochester, N.Y.) were used to produce a high-resolution PA and lateral radiograph of the harvested lumbar spines after biomechanical testing. Radiographs were scanned using image analysis software (Image Pro Plus Software v 5.0, Media Cybernetics, Silver Spring, Md.) running on a Windows XP workstation. A video camera (Model DFC 280, Leica Microsystems, Cambridge, UK) was used to acquire the digital images of the radiographs. These radiographs were also used to gross the samples for histologic analyses as outlined below.

Three blinded evaluators evaluated the resulting Faxitron radiographs for interbody fusion. On the lateral radiographs, the center of the disc space as well as the anterior and posterior margins were evaluated for fusion based on the following scoring method: 4=continuous bony bridging, 3=increased bone density, 2=lucency with some bony bridging, and 1=non-fusion. Lastly, based on both the P/A and lateral radiographs, the blinded evaluators rated an overall fusion score for the spinal level using the following criteria:

3=Solid interbody fusion with no radiolucencies in interbody space
2=Probable fusion with radiolucencies in the interbody space
1=Non-fusion with significant radiolucencies in the disc space with no evidence of superior to inferior bony bridging 3. Undecalcified Histology and Microradiography:

Processing and Stained Undecalcified Sections

In all of the treatment groups, the bisected spinal level was analyzed using undecalcified techniques (microradiography and multiple stain). Differential staining along with qualitative optical microscopy was performed to assess bony bridging and extent of fusion associated with the autograft or the bone graft substitute packed within the PEEK spacers. Differential staining was used to evaluate the extent of fusion adjacent to and within the peek spacers, the host response to the PEEK spacer and bone graft substitute material (if present), the interface of the PEEK spacer, bone graft and substitute incorporation, and bone remodeling within the fusion mass.

After Faxitron radiography, all spinal levels containing an implant were grossed in the following manner. Using the band saw, a coronal plane cut was made along the entire length of the spinal column at the anterior aspect of the pedicles leaving anterior tissues intact. Tissues posterior to the disc space were discarded. Next, the anterior column of the spinal level was bisected mid-sagittally to produce right and left halves. The entire disc space was left intact. The inferior half of the L4 anterior column adjacent to the treated level was retained. The superior half of the L5 anterior column adjacent to the treated level was retained. Right and left sagittal samples from the level were so labeled, fixed in formalin, and processed (sequentially dehydrated in alcohols, cleared in a xylene substitute, and embedded in graded catalyzed methyl methacrylate.

After polymerization was complete and the samples hardened, sectioning and staining was performed. The blocks containing the right and left halves of the treated aspect of the spinal level were sectioned in the sagittal plane on a low speed diamond saw (Buehler Isomet, Lake Bluff, Ill.). For all embedded tissue blocks, sagittal sectioning commenced from the middle of the treated aspect of the spinal level to the lateral aspect of the treated area. Thus, section #1 from the "right block" is sampled in the middle of the fusion mass whereas section #6 from the "right block" is sampled at the far lateral aspect of the treated area. Weights were used to produce sections on the order of 300 µm. Approximately 5-10 sections were made in the sagittal plane through each half of the interbody space. If necessary, grinding was performed to obtain the desired thickness. The thickness of the sections was measured with a metric micrometer (Fowler, Japan). Differential staining using a trichrome stain was used to permit histological differentiation.

Stained undecalcified sections were scanned using image analysis software (Image Pro Plus Software v 5.0, Media Cybernetics, Silver Spring, Md.) running on a Windows XP workstation. A video camera (Model DFC 280, Leica Microsystems, Cambridge, UK) was used to acquire the digital images of the stained undecalcified sections.

Section Fusion Criteria: Undecalcified sections were evaluated for fusion in the center of the disc space or thrugrowth region of the device, in the anterior margin, and in the posterior margin. These anatomic locations for each section were considered to be fused only if continuous bony bridging was found from superior to inferior.

Level Fusion Criteria: Based on all sections evaluated, the following criteria were used to determine if histologic fusion was present in the level. The spinal level was considered fused if greater than 50% of the sections (corresponding microradiographs were analyzed concurrently but not "counted twice" for fusion) showed continuous bony bridging. A partial fusion existed if less than 50% of the sections (and corresponding microradiographs) showed continuous bony bridging. A non-fusion existed if none of the sections and corresponding microradiographs showed continuous bony bridging.

Microradiography

Undecalcified sections from the treated lumbar spinal levels were radiographed using a microradiography unit (Faxitron radiography unit, Hewlett Packard, McMinnville, Oreg.) and spectroscopic film (B/RA 4153 film, Kodak, Rochester, N.Y.). The thickness of the sections was measured with a metric micrometer (Fowler, Japan) to determine the exposure time. Sections were labeled with ultra-fine permanent markers, placed on the Ektascan B/RA 4153 film, and exposed to the x-ray source at 20 kV and 3 mA for approximately 45 seconds for each 100 µm of section thickness. The film was then developed, fixed, and analyzed for ossification using standard optical microscopy. Microradiographs were scanned using image analysis software (Image Pro Plus Software v 5.0, Media Cybernetics, Silver Spring, Md.) running on a Windows XP workstation. A video camera (Model DFC 280, Leica Microsystems, Cambridge, UK) was used to acquire the digital images of the microradiographs.

Analysis of the sections and microradiographs was used to:
1) Evaluate the extent of fusion adjacent to and within the peek spacers, bone graft and substitute incorporation, and bone remodeling within the fusion mass,
2) Determine the host response to the biomaterials used, and
3) Evaluate the interface of the PEEK spacer.

Results

1. Radiographic Evaluation

Good radiographic fusion scores were obtained in both treated groups, with the Inventive Putty+BMP2+PEEK group performing slightly better than the autograft group (average 2.8 versus 2.4, Table 1). To study if relationships existed between the radiographic fusion score and treatment, a contingency table was generated (Table 2), and chi-square analysis was conducted. As seen in Table 2, the frequency for achieving a fusion score of 3 (Solid Fusion) was 56% for the Autograft+PEEK group and 83% for the Inventive Putty+BMP2+PEEK group. The frequency for achieving a fusion score of 2 (Probable Fusion) and up was 83% for the Autograft+PEEK group and 100% for the Inventive Putty+BMP2+PEEK group. Chi-square analysis showed that a trend existed (p<0.11) for the Inventive Putty+BMP2+PEEK group to achieve higher radiographic fusion score than the Autograft+PEEK group.

TABLE 1

Average Radiographic Fusion Scores for Each Group

| Treatment Groups | Fusion Score |
| --- | --- |
| Autograft + PEEK (n = 6) | 2.4 |
| IP + BMP2 + PEEK (n = 6) | 2.8 |

TABLE 2

Observed frequencies of overall radiographic fusion scores for the treatment groups.

| | Total Count for Score 3 | Total Count for Score 2 | Total Count for Score 1 | Percentile Frequency for Score 3 | Percentile Frequency for Score 2+ |
| --- | --- | --- | --- | --- | --- |
| Autograft + PEEK | 10 | 5 | 3 | 56% | 83% |
| IP + BMP2 + PEEK | 15 | 3 | 0 | 83% | 100% |

2. Biomechanics Results

Figure 3:
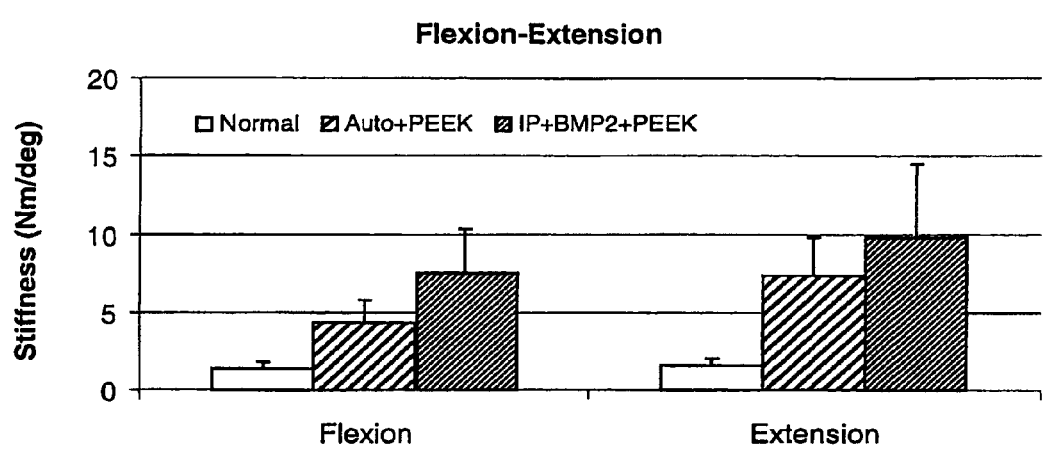
FIG. 3 provides a chart showing the average flexibility of the normal intact and two treated groups in flexion and extension loads, as described in Example 2 below.
Figure 4:
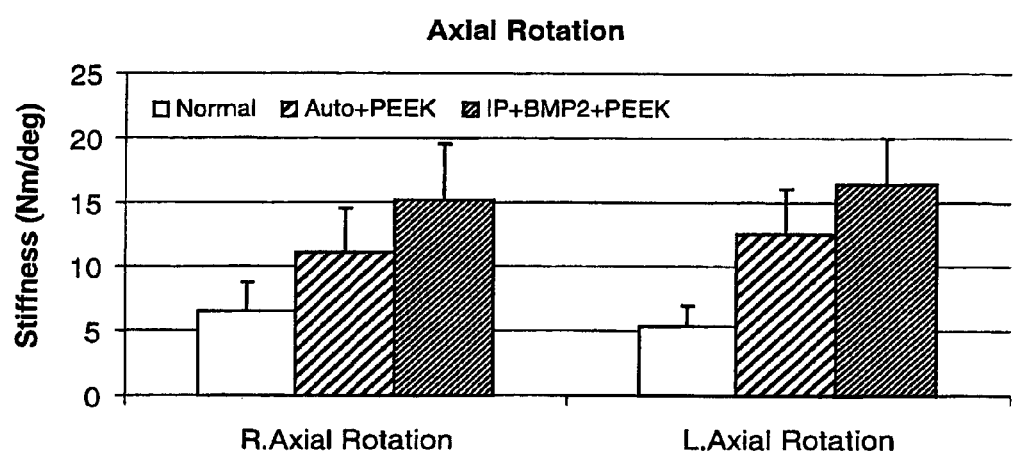
FIG. 4 provides a chart showing the average flexibility of the normal intact and two treated groups in right and left axial rotation loads, as described in Example 2 below.
Figure 5:
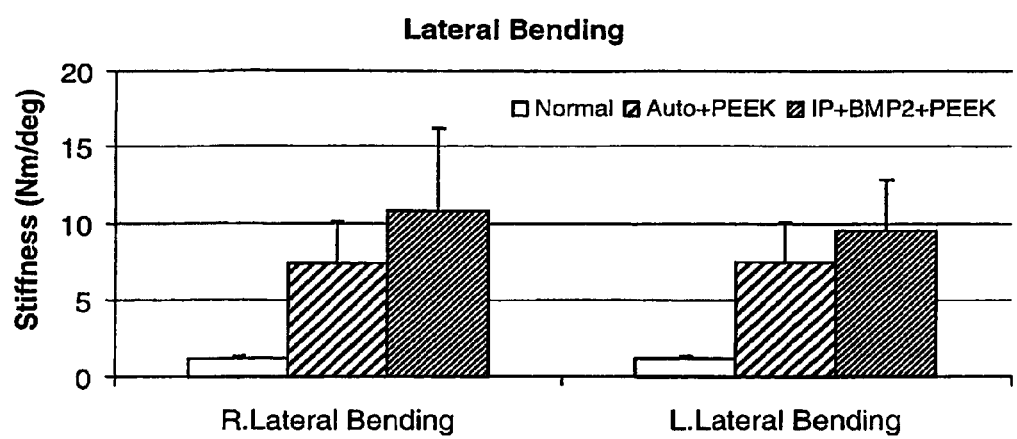
FIG. 5 provides a chart showing the average flexibility of the normal intact and two treated groups in right and left lateral bending loads, as described in Example 2 below.

The mean stiffness in the six loading directions for the two treated interbody fusion groups as well as an intact normal group is shown in FIGS. 3 through 5. In particular, FIG. 3 provides a chart showing the average flexibility of the normal intact and two treated groups in flexion and extension loads. Differences between treated groups and the normal intact group were statistically significant in both directions. The difference between the two treated groups was significant in flexion only. FIG. 4 provides a chart showing the average flexibility of the normal intact and two treated groups in right and left axial rotation loads. Differences between treated groups and the normal intact group were statistically significant in both loading directions, whereas differences between the two treated groups were not statistically significant. FIG. 5 provides a chart showing the average flexibility of the normal intact and two treated groups in right and left lateral bending loads. Differences between treated groups and the normal intact group were statistically significant in both loading directions, whereas differences between the two treated groups were not statistically significant.

On average, level stiffness of the two treated groups was 3.1 (Autograft+PEEK group) and 5.4 (Inventive Putty+BMP2+PEEK group) times stiffer than the normal intact group in flexion (p<0.0001), 4.6 (Autograft+PEEK group) and 6.1 (Inventive Putty+BMP2+PEEK group) times stiffer than the normal intact group in extension (p<0.0001). Both treated groups were 1.7 to 3.0 times stiffer than the normal intact group in axial rotation (P<0.0004), and 6.3 to 9.3 stiffer than the normal intact group in lateral bending (p<0.0001). Comparing flexibility of the two treated groups, Inventive Putty+BMP2+PEEK group was stiffer on average in every loading direction. Statistically significant differences were only found in flexion (74% stiffer, p<0.002).

EXAMPLE 3

Use of Inventive Putty in Posterolateral Fusions

An instrumented ovine posterolateral fusion model was used to evaluate the ability of Autograft and the Inventive Putty of Example 1+rhBMP-2 (IP+rhBMP-2) to effect posterolateral fusion at 6 months post-operatively. The efficacy of these treatments to induce posterolateral fusion in the ovine lumbar fusion model was evaluated using blinded radiographic, biomechanical, and histologic measures. Assessment of fusion was made with Faxitron high-resolution radiography, non-destructive biomechanical testing, and undecalcified histology with microradiography. All analyses were conducted in a blinded fashion. In addition, undecalcified histology was used to evaluate the osteocompatibility of the bone graft substitutes. In addition to the treatment groups being evaluated, biomechanical properties of normal spines were evaluated using the same methodology. When all data acquisition was complete, the key was broken, and radiographic, biomechanic, and histologic data were analyzed by treatment group.

Animal Model:

The sheep lumbar spine model was used because of the biomechanical similarities between the sheep and human lumbar spine. Wilke et al. characterized the biomechanical parameters (range of motion, neutral zone, and level stiffness) of sheep spines and made comparisons with data from human specimens previously published by White and Panjabi (see, Wilke et al., *Spine:* 22(20): 2365-2374, 1997; and White AA and Panjabi M M, editors, Clinical Biomechanics of the Spine, 2nd ed., J. B. Lippincott, Philadelphia, Pa., 1990). Wilke et al. found that the "ranges of motion of sheep spines for the different load directions are qualitatively similar in their craniocaudal trends to those of human specimens reported in the literature." They further concluded that: "Based on the biomechanical similarities of the sheep and human spines demonstrated in this study, it appears that the sheep spine . . . can serve as an alternative for the evaluation of spinal implants.

Surgical Technique:

Upon arrival at the facility, the 12 sheep were placed in the appropriate pastures of the large animal research barn. They were dewormed and eartagged for identification. Physical examination was performed and any animals with signs of respiratory disease had venous blood submitted for a complete blood count (CBC).

The sheep were anesthetized. Wool was removed from the dorsal lumbar area and the sheep positioned in sternal recumbency on the operating table. The dorsal and dorsolateral lumbar area were prepared for aseptic surgery with multiple scrubs of povidone-iodine alternated with isopropyl alcohol. The area was draped and a dorsal approach to L3-L6 was made through the dorsal lumbar musculature.

Iliac Crest Autograft Harvesting: Autograft was used as a control. The following protocol was followed. The dorsal and dorsolateral lumbar and iliac crest areas were prepared for aseptic surgery with multiple scrubs of povidone-iodine alternated with isopropyl alcohol. The area was draped and a 3-cm incision made over the left iliac crest. Following partial reflection of the gluteal muscles. An osteotome was used to create a small window in the craniodorsal face of the iliac crest. Using a curette, about 2 cc of autogenous cancellous bone was removed, and was later packed into one of the implants (e.g. PEEK spacer) used for the lumbar fusion (this is the control case). Intralesional morphine sulfate was administered prior to closure of the iliac crest incision. The iliac crest site was closed routinely using 2/0 polysorb for the subcutaneous tissues and stainless steel staples for the skin.

Dorsolateral ("posterolateral") Interbody Fusion: The dorsal lumbar area was prepared for aseptic surgery with multiple scrubs of povidone-iodine alternated with isopropyl alcohol. The area was draped and local anesthesia (Bupivicaine) was infiltrated along the site of the intended incision for the dorsal approach to L3 and L4 and spinous processes.

Approach to the transverse processes: A 20 cm. skin incision is made and the paraspinal muscles are dissected off the spinous processes and laminae. Facet joints and transverse processes between L3 and L4 are exposed.

Instrumentation and Spine fusion Technique: The transverse processes of L3 and L4 were decorticated bilaterally. The bone graft from the iliac crest or a bone graft substitute that is being investigated (rhBMP-2+Inventive Putty), was now placed between the transverse processes (~10 cc per side). The sheep now underwent transpedicular screw fixation using screws and rods. The pedicle screws and rods were inserted at this point in the procedure.

Wound Closure: Routine closure of external abdominal muscular fascia (0 Polysorb (absorbable suture), subcutaneous tissue (2/0 Polysorb and skin (2/0 monofilament non-absorbable suture) was performed. Operative time for each animal was usually about 50 minutes. Perioperative antibiotics (Cephazolin sodium) were administered. Postoperative radiographs were performed while the sheep were still under general anesthesia.

Aftercare: Immediately after surgery, the sheep were transferred from the operating table to a modified wheelbarrow and while still under general anesthesia, taken to the radiology suite where dorsoventral and lateral radiographs of the fusion sites were obtained. Following radiographic evaluation, while still in the modified wheelbarrow, they were observed until the swallowing reflex returns. At that point they were extubated and taken to a trailer where they were propped in sternal recumbency. At the end of the day, all animals that were operated upon that day were moved to research pastures. The sheep were housed outdoors (with access to a three-sided shelter) for the convalescence and allowed to exercise at will. Postoperative analgesia was provided as described. The sheep were anesthetized and radiographed at three months posoperatively.

Euthanasia: After 6 months postoperatively, the 12 sheep were euthanized in a humane manner. Euthanasia was performed according to the guidelines set forth by the AVMA Panel on Euthanasia (J. Am. Vet. Med. Assoc., 202:229-249, 1993). Radiographs of the lumbar fusion sire were taken in these sheep to evaluate the degree of fusion at L3-L4.

Specimen Collection and Handling: Following euthanasia, a complete gross necropsy was conducted on all 12 animals. Conventional gross examination of all major organ systems and histopathological evaluation of any pathological lesions was performed. Animals that died or were prematurely euthanized during the course of the study had a complete necropsy performed to determine the cause of disease or death. At necropsy the lumbar vertebrae that were fused were harvested.

Material Analysis: All samples from the lumbar area from the sheep were subjected to mechanical testing of the fusion sites. They were tested for stiffness to saggital and coronal plan bending moments (flexion, extension, right and left lateral bending). As these mechanical tests were nondestructive, the fusion sites were also examined histologically.

Implant Materials:

The study groups are defined below. An animal from the Autograft group died prematurely and was excluded from all analyses. Therefore the total number of animals from the Autograft group in the results was reduced to 5.

| Study Group (per study design) | | No. of Samples (N) |
|---|---|---|
| 1) | 10 cc/side Autograft (Autograft) | 6 |
| 2) | Inventive Putty + rhBMP-2 (IP + BMP2) | 6 |
| 3) | Normal Intact | 17 |
| | Total | 28 |

At the completion of the survival phase of the animal study, the spines were immediately frozen for evaluation. The efficacy of the bone graft and bone graft substitutes to effect posterolateral fusion and bony healing was assessed by performing radiographic, biomechanical, and histologic analyses as detailed below. The study was performed in a blinded fashion. After all analyses were completed, the key was broken and radiographic, biomechanical, and histologic data were analyzed by treatment group.

Methods of Analysis:

1. Radiographic Assessment:

Radiographs were taken immediately after surgery, at regular post-operative intervals, and at the time of sacrifice. A Faxitron (Hewlett Packard, McMinnville, Oreg.) high-resolution radiography unit and high-resolution film (EKTASCAN B/RA Film 4153, Kodak, Rochester, N.Y.) was used to produce a high-resolution PA radiograph of the harvested lumbar spines after biomechanical testing. Radiographs were scanned using image analysis software (Image Pro Plus Software v 5.0, Media Cybernetics, Silver Spring, Md.) running on a Windows XP workstation. A video camera (Model DFC 280, Leica Microsystems, Cambridge, UK) was used to acquire the digital images of the radiographs. These radiographs were also used to gross the samples for histologic analyses as outlined below.

Three blinded evaluators evaluated the resulting Faxitron radiographs for intertransverse process fusion. On the PA radiograph, on both the right and left sides of the level, the intertransverse process space was evaluated for fusion based on the following scoring method: 4=continuous bony bridging, 3=increased bone density, 2=lucency with some bony bridging, and 1=non-fusion. Based on both the right and left sides of the PA radiographs, the blinded evaluators rated an overall fusion score for the spinal level using the following criteria:

3=Solid Fusion: Solid intertransverse process fusion on Right AND Left with no radiolucencies 2=Possible Fusion: Intertransverse process fusion on the Right OR Left, but not both. Lucencies in intertransverse process space on right or left.

1=Non-Fusion: Isolated bone formation without continuous superior to inferior bony bridging on both right and left sides. Significant lucency with no evidence of intertransverse process fusion on the right or left.

After the treatment code was broken, the radiographic fusion data were statistically analyzed.

2. Ex-vivo Biomechanical Testing of the Treated Lumbar Motion Segment:

Flexibility Testing:

Unconstrained biomechanical testing was performed in a non-destructive manner on all spines after the frozen specimens were thawed. All metallic posterior instrumentation used to stabilize the posterolateral fusion was removed prior to biomechanical testing so that the stiffness of the spine and fusion mass construct was tested. Flexibility of the motion segments was determined in flexion, extension, right and left lateral bending, and right and left axial rotation. All tests were performed within 12 hours of specimen thawing. Specimens were only frozen once. The purpose of the biomechanical testing was to quantify the stiffness of the lumbar motion segments augmented with the previously described fusion treatments. The treated (L4-L5) motion segments were dissected from the harvested lumbar spines and cleaned of extraneous soft tissue leaving the ligamentous and osseous tissues intact. Specially designed loading and base frames were secured on the L4 and L5 vertebra, respectively.

Moments of 0, 0.5, 2.5, 4.5, 6.5, and 8.5 Nm were achieved in each loading direction. Static loads were used to apply the pure moments. A six-degree of freedom load cell was placed in series with the tested specimen to verify the applied moments. Three markers reflecting the infrared light were attached to each vertebra. The locations of the infrared reflective markers were recorded using three VICON cameras (Vicon Peak, Oxford, England) at each load. Three-dimensional load-displacement data were then acquired with pure moments applied in flexion, extension, left and right lateral bending, and left and right axial rotation. The three-dimensional coordinate data were analyzed to obtain the rotation angles of the superior vertebra with respect to the inferior vertebra and rotational flexibility of each motion segment.

Biomechanics data from a normal (untreated) intact group of sheep lumbar spine motion segments that have been obtained previously were used as baseline data for normal lumbar spine motion for L4-L5 in sheep. Differences in the stiffness (flexibility) between groups and the normals were statistically compared. Non-parametric Kruskal-Wallis and Mann-Whitney tests were used to analyze the biomechanics data.

3. Undecalcified Histology and Microradiography:

Processing and Stained Undecalcified Sections: In each of the treatment groups, the bisected spinal intertransverse process spaces were analyzed using undecalcified techniques (microradiography and multiple stain). Differential staining along with qualitative optical microscopy was performed to assess bony bridging and extent of fusion associated with autograft and the bone graft substitutes. Differential staining was used to evaluate the host response to the bone graft substitutes.

After Faxitron radiography, all spinal levels containing an implant were grossed in the following manner. The superior (L3-L4) and inferior (L5-L6) disc spaces were transected leaving the treated (L4-L5) functional spinal unit (FSU) intact. Using the band saw, a coronal plane cut was made along the entire length of the spinal column at the anterior aspect of the pedicles leaving posterior tissues intact. Anterior tissues were discarded. Next, the posterior elements of the spinal level were bisected mid-sagittally to produce right and left halves. An angled cut in the axial plane was made so that tissues cranial to the cranial transverse processes were discarded on the right and left sides. An angled cut in the axial plane was made so that tissues caudal to the caudal transverse processes were trimmed and discarded on the right and left sides. Tissues in the Right and Left intertransverse process spaces were further divided in the sagittal plane to produce a medial and lateral sample of the Left fusion mass as well as a medial and lateral sample of the Right fusion mass. Right and left medial and lateral samples were so labeled, fixed in formalin, and processed (sequentially dehydrated in alcohols, cleared in xylene or xylene substitute, and embedded in graded catalyzed methyl methacrylate).

After polymerization was complete and the samples hardened, sectioning and staining was performed. The blocks containing the transverse processes, graft and graft substitutes, and tissues in the transverse process space were sectioned in the sagittal plane on a low speed diamond saw (Buehler Isomet, Lake Bluff, Ill.). For the medial and lateral embedded tissue blocks described above, sectioning commenced from the middle of the fusion mass for both the medial and lateral blocks. Thus, section #1 from the "right lateral block" is sampled in the middle of the fusion mass whereas section #6 from the "right lateral block" is sampled at the far lateral anatomic aspect of the fusion mass (tips of the transverse processes). Similarly, section #1 from the "right medial block" is sampled in the middle of the fusion mass whereas section #6 from the "right medial block" is sampled at the far medial anatomic aspect of the fusion mass (lamina and facet joints). Weights were used to produce sections on the order of 300 µm. Approximately 5-10 sections were made in the sagittal plane through each half of the intertransverse process space. If necessary, grinding was performed to obtain the desired thickness. The thickness of the sections was measured with a metric micrometer (Fowler, Japan). Differential staining using a trichrome stain was used to permit histological differentiation.

Stained undecalcified sections were scanned using image analysis software (Image Pro Plus Software v 5.0, Media Cybernetics, Silver Spring, Md.) running on a Windows XP workstation. A video camera (Model DFC 280, Leica Microsystems, Cambridge, UK) was used to acquire the digital images of the stained undecalcified sections. Undecalcified histology sections and microradiographs for this study were scanned so that dorsal was at the top of the image. The ventral side of the section was usually flat and showed two oval transverse processes. Sections were scanned so that transverse processes were at the bottom (ventral aspect) of the image. A mm. scale was scanned at the bottom (ventral aspect) of the image. Microsoft Photo editor was used to crop the images.

Section Fusion Criteria: Undecalcified sections were considered fused if continuous bony bridging was found from superior to inferior in the section. If the presence of non-osseous tissues obviated continuous bony bridging, the section was further evaluated as follows. For non-fused sections, sections were classified as A) non-fusion with incomplete bridge, but with de novo bone found in >50% of the length of the section, or B) non-fusion with incomplete bridge, with de novo bone found in <50% of the length of the section.

Right and Left Side Level Fusion Criteria: Based on all sections evaluated, the following criteria were used to determine if histologic fusion was present on the right or left side of the level. The right or left side of the spinal level was considered fused if greater than 50% (>50%) of the sections and corresponding microradiographs showed continuous bony bridging. A partial fusion existed if 50% or less (≤50%) of the sections and corresponding microradiographs from the right or left side of the spinal level showed continuous bony bridging. A non-fusion existed if none of the sections and corresponding microradiographs from the right or left side of the spinal level showed continuous bony bridging.

Microradiography: Undecalcified sections from the treated lumbar spinal levels were radiographed using a microradiography unit (Faxitron radiography unit, Hewlett Packard, McMinnville, Oreg.) and spectroscopic film (B/RA 4153 film, Kodak, Rochester, N.Y.). The thickness of the sections was measured with a metric micrometer (Fowler, Japan) to determine the exposure time. Sections were labeled with ultra-fine permanent markers, placed on the Ektascan B/RA 4153 film, and exposed to the x-ray source at 20 kV and 3 mA for approximately 45 seconds for each 100 μm of section thickness. The film was then developed, fixed, and analyzed for ossification using standard optical microscopy. Microradiographs were scanned using image analysis software (Image Pro Plus Software v 5.0, Media Cybernetics, Silver Spring, Md.) running on a Windows XP workstation. A video camera (Model DFC 280, Leica Microsystems, Cambridge, UK) was used to acquire the digital images of the microradiographs.

Analysis of the sections and microradiographs was used to:
1) Evaluate histologic fusion,
2) Determine the host response to the autograft and bone graft substitutes, and
3) Estimate the quality and quantity of bone in the fusion mass within the intertransverse process space.

Results

1. Radiographic Results

The average radiographic fusion scores for the treated groups are presented in Table 3. The Inventive Putty+rhBMP-2 group achieved an average fusion score of 2.7. The average fusion score for the Autograft group was 2.2.

The effect of treatment on the radiographic fusion score was further analyzed. A contingency table was generated (Table 4), and chi-square analysis was conducted. As seen in Table 4, the frequency for achieving a fusion score of 3 (Solid Fusion) was 67% for the Inventive Putty+BMP-2 group and, 40% for the Autograft group. The frequency for achieving a fusion score of 2 (Probable Fusion) and up was 100% for the Inventive Putty+BMP-2 group and 80% for the Autograft group. The difference between the Inventive Putty+BMP-2 group and the Autograft group was not statistically significant (p<0.09).

TABLE 3

Average Radiographic Fusion Scores for Each Group

| Treatment Groups | Fusion Score |
| --- | --- |
| Autograft (n = 5) | 2.2 |
| IP + BMP-2 (n = 6) | 2.7 |

TABLE 4

Observed frequencies of overall radiographic fusion scores for the treatment groups.

| | Total Count for Score 3 | Total Count for Score 2 | Total Count for Score 1 | Percentile Frequency for Score 3 | Percentile Frequency for Score 2+ |
| --- | --- | --- | --- | --- | --- |
| Autograft | 6 | 6 | 3 | 40% | 80% |
| IP + BMP-2 | 12 | 6 | 0 | 67% | 100% |

2. Biomechanics Results

Figure 6:
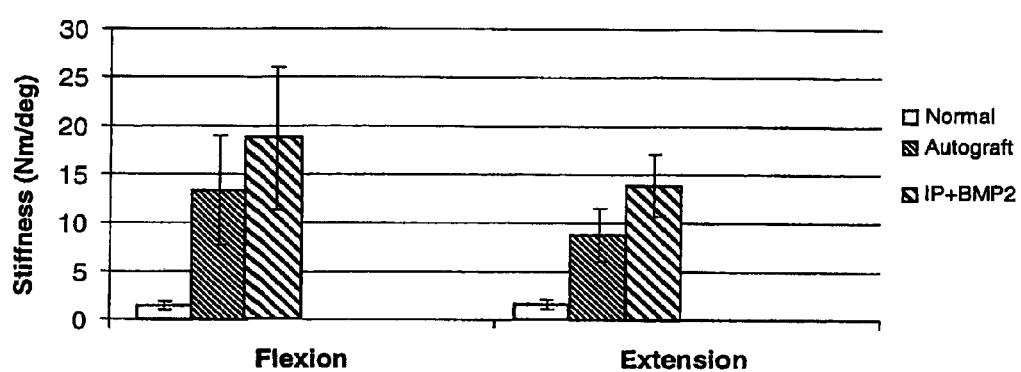
FIG. 6 provides a chart showing the average stiffness of the intact and treated animal groups under flexion and extension loads, as described in Example 3 below.
Figure 7:
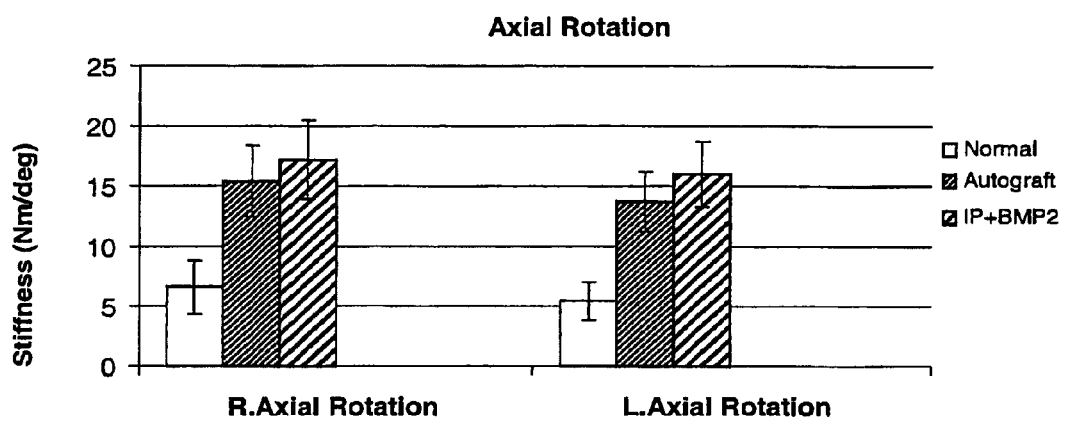
FIG. 7 provides a chart showing the average stiffness of the intact and treated animal groups under axial rotation loads, as described in Example 3 below.
Figure 8:
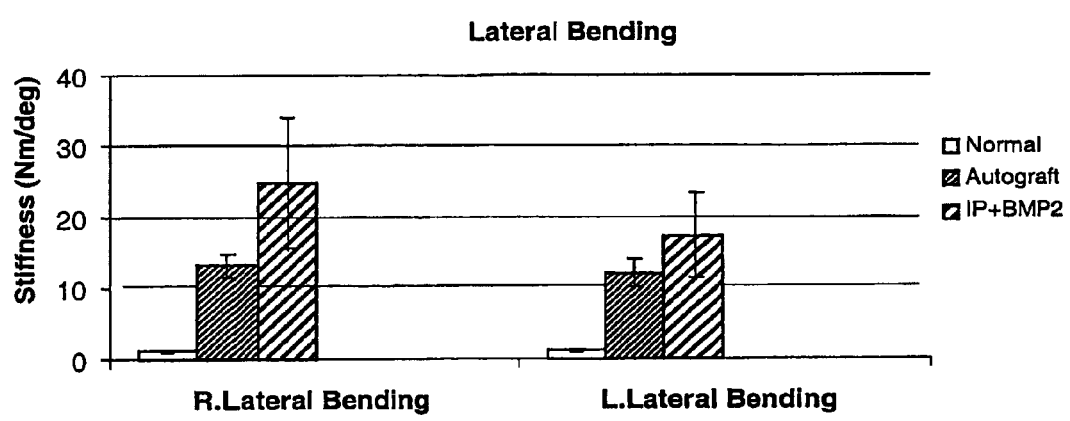
FIG. 8 provides a chart showing the average stiffness of the intact and treated animal groups under lateral bending loads, as described in Example 3 below.

Group stiffness for the treatment groups for axial rotation, lateral bending, flexion and extension are seen in FIGS. 6 through 8. In particular, FIG. 6 provides a chart showing the average stiffness of the intact and treated animal groups under flexion and extension loads, FIG. 7 provides a chart showing the average stiffness of the intact and treated animal groups under axial rotation loads, and FIG. 8 provides a chart showing the average stiffness of the intact and treated animal groups under lateral bending loads. The error bars in these Figures indicate the standard deviations.

Compared to the normal intact spines, the fusion segments from the treatment groups were statistically stiffer in all loading directions. Statistical comparison between the two treated groups showed that the only statistically significant difference was found in the loading direction of right lateral bending (Kruskal-Wallis test, p<0.003). Further Mann-Whitney post-hoc tests showed that the flexibility of the Inventive Putty+BMP2 treated group in right lateral bending was significantly stiffer than the Autograft treated group (87% stiffer, p<0.002).

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. An implantable osteogenic medical implant, comprising: a malleable, cohesive, shape-retaining putty comprising 60% to 75% by weight of an aqueous liquid medium and including a bone morphogenic protein incorporated at a level of about 0.6 mg/cc to about 2 mg/cc of the putty; said putty including mineral particles dispersed therein having an average particle diameter in the range of 0.4 mm to 5 mm at a level of 0.25 g/cc to 0.35 g/cc in the putty, the mineral particles comprising a synthetic ceramic; said putty further including insoluble collagen fibers at a level of 0.04 g/cc to 0.1 g/cc of the putty, wherein the mineral particles form a scaffold for bone ingrowth and comprise biphasic calcium phosphate that has a tricalcium phosphate: hydroxyapatite weight ratio of 50:50 to 95:5 and a weight ratio of insoluble collagen fibers to soluble collagen in the material is at a range of 4:1 to 1:1.

2. The implantable osteogenic medical implant of claim 1, wherein said putty is comprised of about 65% to about 75% of water.

3. The implantable osteogenic medical implant of claim 1, wherein said weight ratio of insoluble collagen fibers to soluble collagen in the putty is in the range of about 75:25 to about 60:40.

4. The implantable osteogenic medical implant of claim 1, wherein said bone morphogenic protein comprises BMP-2.

5. The implantable osteogenic medical implant of claim 4, wherein said BMP-2 comprises recombinant human BMP-2.

6. The implantable osteogenic medical implant of claim 1, wherein said insoluble collagen fibers are present in said putty at a level of 0.05 g/cc to 0.08 g/cc.

7. The implantable osteogenic medical implant of claim 1, wherein said mineral particles have an average particle diameter in the range of about 0.4 to about 3.0 mm.

8. The implantable osteogenic medical implant of claim 1, wherein said mineral particles have an average particle diameter in the range of about 0.4 to about 2.0 mm.

9. The implantable osteogenic medical implant of claim 1, wherein: said weight ratio of insoluble collagen fibers to soluble collagen is about 75:25 to about 65:35; said mineral particles have an average particle diameter in the range of about 0.4 to about 4.0 mm; said putty includes the insoluble collagen fibers at a level of about 0.05 to 0.08 g/cc; and said bone morphogenic protein is incorporated at a level of about 0.8 mg/cc to about 1.8 mg/cc of the putty.

10. The implantable osteogenic medical implant of claim 9, wherein said bone morphogenic protein comprises recombinant human BMP-2.

\* \* \* \* \*

UNITED STATES PATENT AND TRADEMARK OFFICE
CERTIFICATE OF CORRECTION

| | | |
|---|---|---|
| PATENT NO. | : 8,734,835 B2 | Page 1 of 1 |
| APPLICATION NO. | : 13/015953 | |
| DATED | : May 27, 2014 | |
| INVENTOR(S) | : McKay et al. | |

It is certified that error appears in the above-identified patent and that said Letters Patent is hereby corrected as shown below:

On the Title Page, in item (56), under "OTHER PUBLICATIONS", in Column 2, Line 3, delete "salesandmarketinqnetwork.com/" and insert -- salesandmarketingnetwork.com/ --, therefor.

On the Title Page, in the illustrative Figure, delete Main Designator "1" and insert Main Designator -- 11 --, therefor.

In the Drawings;

In Fig. 1, Sheet 1 of 8, delete Main Designator "1" and insert Main Designator -- 11 --, therefor.

In the Specification;

In Column 11, Line 35, delete "suture)," and insert -- suture)), --, therefor.

In Column 11, Line 37, delete "suture)" and insert -- suture)) --, therefor.

In Column 13, Line 39, delete "(microradiography" and insert -- (microradiographs --, therefor.

In Column 13, Line 64, delete "methacrylate." and insert -- methacrylate). --, therefor.

In Column 17, Line 25, delete "suture)," and insert -- suture)), --, therefor.

In Column 17, Line 27, delete "suture)" and insert -- suture)) --, therefor.

In Column 19, Line 49, delete "(microradiography" and insert -- (microradiographs --, therefor.

Signed and Sealed this
Fourth Day of November, 2014

Michelle K. Lee
*Deputy Director of the United States Patent and Trademark Office*